[19] United States Patent
Fothergill et al.

[11] 4,395,559
[45] Jul. 26, 1983

[54] 2,3-INDOLEDIONE DERIVATIVES

[75] Inventors: Graham A. Fothergill, Knebworth; John M. Osbond, Hatfield, both of England

[73] Assignee: Hoffmann-La Roche Inc., Nutley, N.J.

[21] Appl. No.: 211,883

[22] Filed: Dec. 1, 1980

[30] Foreign Application Priority Data

Dec. 12, 1979 [GB] United Kingdom ............... 7942324

[51] Int. Cl.$^3$ ..................... A61K 31/40; C07D 209/38
[52] U.S. Cl. .................................. 548/485; 424/274; 548/467; 564/214; 564/391; 564/443
[58] Field of Search ................... 260/325 R; 548/485

[56] References Cited
U.S. PATENT DOCUMENTS 1,778,174 10/1930 Thiess et al. ................. 260/325 R
3,825,558 7/1974 Seemann ..................... 260/325 R
4,137,331 1/1979 Berthold et al. ............. 260/325 R
4,212,804 7/1980 Coppola ..................... 260/325 R

FOREIGN PATENT DOCUMENTS 1069343 5/1967 United Kingdom .............. 564/349

Primary Examiner—Alton D. Rollins
Attorney, Agent, or Firm—Jon S. Saxe; Bernard S. Leon; William G. Isgro

[57] ABSTRACT 2,3-Indoledione derivatives of the formula

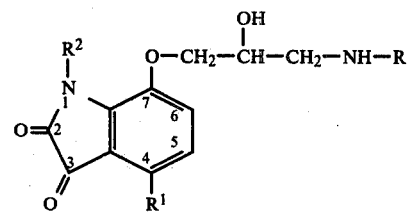

wherein R is isopropyl or tert.butyl, $R^1$ is hydrogen or lower alkyl and $R^2$ is lower alkyl or lower aralkyl, and their pharmaceutically acceptable acid addition salts, prepared from a compound of the formula

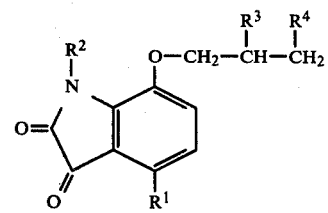

wherein $R^3$ is hydroxy and $R^4$ is chlorine or bromine or $R^3$ and $R^4$, taken together, are oxygen, and $R^1$ and $R^2$ are as previously set forth, are described. The compounds of formula I and their pharmaceutically acceptable addition salts are useful as $\beta$-adrenergic blocking agents and antihypertensive agents.

7 Claims, No Drawings

2,3-INDOLEDIONE DERIVATIVES

BRIEF SUMMARY OF THE INVENTION

This invention relates to a compound of the formula

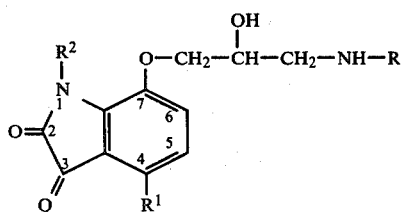

wherein R is isopropyl or tert.butyl, $R^1$ is hydrogen or lower alkyl and $R^2$ is lower alkyl or lower aralkyl, and a pharmaceutically acceptable salt thereof, prepared by treating a compound of the formula

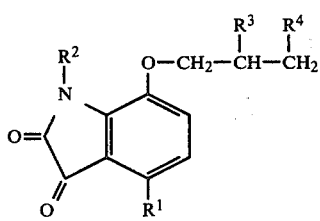

wherein $R^3$ is hydroxy and $R^4$ is chlorine or bromine or $R^3$ and $R^4$, taken together, are oxygen, and $R^1$ and $R^2$ are as previously set forth, with an amine of the formula $$H_2N-R \qquad III$$

wherein R is as previously described, if desired, resolving an obtained racemate into the two antipodes and, if desired converting the resulting compound of formula I into a pharmaceutically acceptable addition salt.

DETAILED DESCRIPTION OF THE INVENTION

The 2,3-indoledione derivatives of the invention are compounds of the formula

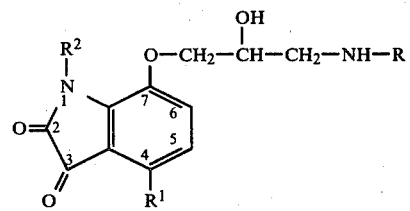

wherein R is isopropyl or tert.butyl, $R^1$ is hydrogen or lower alkyl and $R^2$ is lower alkyl or lower aralkyl, and their pharmaceutically acceptable acid addition salts.

As used herein, the term "lower alkyl" denotes a straight-chain or branched-chain alkyl which preferably contains from 1 to 6 carbon atoms, for example, methyl, ethyl, propyl, isopropyl, butyl, isobutyl, tert.butyl, pentyl, hexyl, and the like. The term "lower aralkyl", as used herein, denotes a lower alkyl, as described earlier, in which one of the hydrogen atoms has been replaced by an aryl group. Exemplary of lower aralkyl in benzyl, β-phenethyl, or the like.

A preferred class of 2,3-indoledione derivatives provided by the invention comprises a compound of formula I wherein $R^1$ is hydrogen and $R^2$ is lower alkyl, or its pharmaceutically acceptable acid addition salt.

Examples of preferred compounds of formula I are:
7-(3-Tert.butylamino-2-hydroxypropoxy)-1-methyl-2,3-indoledione;
7-(3-Tert.butylamino-2-hydroxypropoxy)-1,4-dimethyl-2,3-indoledione;
7-(2-Hydroxy-3-isopropylaminopropoxy)-1,4-dimethyl-2,3-indoledione; and
1-Benzyl-7-(3-tert.butylamino-2-hydroxypropoxy)-4-methyl-2,3-indoledione.

According to the process of the invention, the 2,3-indoledione derivatives, that is, the compounds of formula I and their pharmaceutically acceptable acid addition salts can be prepared by (a) reacting a compound of the formula

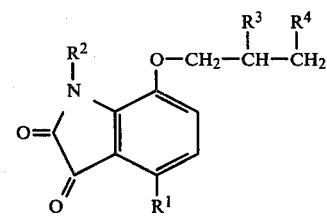

wherein $R^3$ is hydroxy and $R^4$ is chlorine or bromine, or $R^3$ and $R^4$, when taken together, are oxygen and $R^1$ and $R^2$ are as previously described, with an amine of the formula $$H_2N-R \qquad III$$

wherein R is as previously described, (b) if desired, resolving a racemate obtained into its two anitpodes, and/or (c) if desired, converting the resulting compound of formula I into a pharmaceutically acceptable acid addition salt.

The reaction of a compound of formula II with an amine of formula III, for example, isopropylamine or tert.butylamine, can be carried out in a known manner. The reaction can be carried out in the presence of an inert organic solvent. When an inert organic solvent is used, a lower alkanol, such as, methanol or ethanol, can be suitably used. Alternatively, an excess of the amine of formula III can be used and can serve as the solvent. The treatment is advantageously carried out at a temperature in the range of from about 0° C. to room temperature, preferably at room temperature, and under atmospheric pressure.

The compounds of formula I contain an asymmetric carbon atom and can, therefore, occur in racemic or optically active form. The invention includes within its scope the racemates as well as the optically active forms. A racemate can, if desired, be resolved into the optical isomers in accordance with known methods, for example, by fractional crystallization of a salt formed with an optically active acid.

The compounds of formula I can be converted into pharmaceutically acceptable acid addition salts by treatment with a pharmaceutically acceptable inorganic acid, for example, hydrochloric acid, hydrobromic acid, sulfuric acid, phosphoric acid, or the like, or with a pharmaceutically acceptable organic acid, for example, acetic acid, tartaric acid, citric acid, fumaric acid, maleic acid, malic acid, methanesulfonic acid, paratoluenesulfonic acid, or the like.

The starting materials of formula II can be prepared, for example, in accordance with the Formula Scheme which follows, in which $R^1$ and $R^2$ are as previously described, and $R^5$ is lower alkyl, preferably methyl.

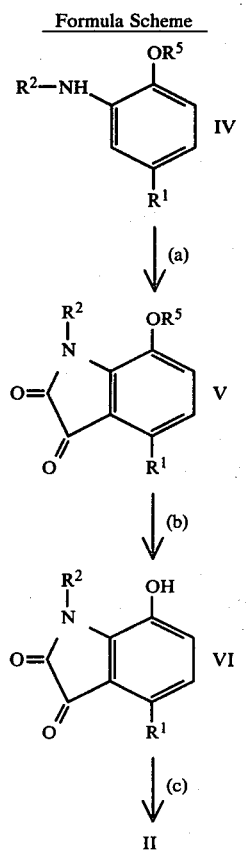

In step (a) of the foregoing Formula Scheme, a compound of formula IV, which is a known compound or an analogue of a known compound readily accessible in a known manner, is converted into a compound of formula V. This conversion is carried out by reacting a compound of formula IV with oxalyl chloride in an inert organic solvent, preferably an aromatic hydrocarbon such as benzene, at a temperature in the range of from about 50° C. to 80° C., and subsequently heating the reaction product at a temperature above about 160° C. in a high-boiling inert organic solvent, preferably a nitrated aromatic hydrocarbon, such as, nitrobenzene, nitrotoluene, or the like.

In step (b) of the Formula Scheme, the lower alkoxy group $OR^5$ is converted into a hydroxy group in a known manner, for example, using boron tribromide at a low temperature, for example, about −70° C., pyridine hydrochloride at a high temperature, for example, about 200° C., or the like. It is understood that when $R^2$ is lower aralkyl, the particular method chosen must be one in which this group is not affected.

In step (c) of the Formula Scheme, a phenol of formula VI is reacted with epichlorohydrin or epibromohydrin, preferably epichlorohydrin, in a known manner. In one embodiment, which is preferred, the reaction is carried out in the presence of a basic anion-exchange resin such as Amberlyst A-26 using an excess of epichlorohydrin or epibromohydrin and at an elevated temperature, for example, at about 60° C. In another embodiment, the reaction can be carried out in the presence of an alkali metal hydroxide, for example, sodium hydroxide or potassium hydroxide, and conveniently in the presence of a water-miscible organic solvent, for example, lower alkanol, such as, methanol or ethanol, at a temperature in the range of from about 0° C. to about room temperature, preferably at room temperature. The resin Amberlyst A-26 referred to herein is a macroreticular ion-exchanger resin containing tetraalkylammonium groups and chlorine anions and having a mesh size of 20–50 mesh.

The product obtained in the foregoing reaction is a mixture of an epoxide of the formula

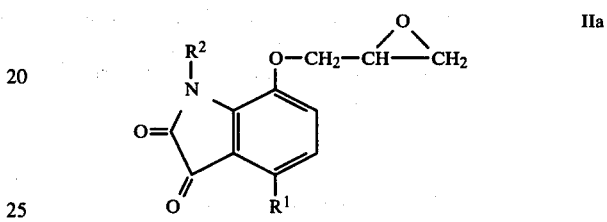

wherein $R^1$ and $R^2$ are as previously described, and the corresponding chlorohydrin or bromohydrin of the formula

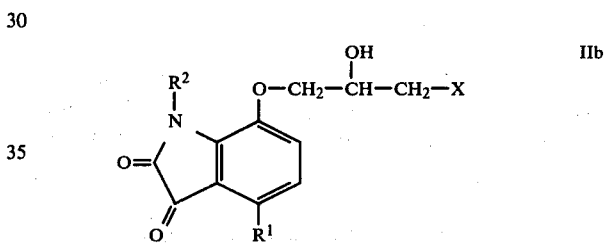

wherein $R^1$ and $R^2$ are as previously described, and X is chlorine or bromine. The chlorohydrin or bromohydrin of formula IIb normally is present in minor amounts.

The 2,3-indoledione derivatives provided by the invention, that is, the compounds of formula I and their pharmaceutically acceptable acid addition salts, possess β-adrenergic blocking activity. Accordingly, they can be used for the treatment and prophylaxis of diseases of the heart, such as, for example, angina pectoris and cardiac arrhythmias. They may also be used as antihypertensive agents.

The β-adrenergic blocking activity of the 2,3-indoledione derivatives of formula I can be demonstrated using standard test procedures. In one such test procedure, the β-adrenergic blocking acitivity is demonstrated in rats by determining the dosage in μg/kg i.v. of substance being tested which is required to produce a 50% reduction in isoprenaline-induced tachycardia, this dosage being expressed as the $ED_{50}$. In this test, 7-(3-tert.butylamino-2-hydroxypropoxy)-1-methyl-2,3-indoledione hydrochloride, 7-(3-tert.butylamino-2-hydroxypropoxy)-1,4-dimethyl-2,3-indoledione hydrochloride and 7-(2-hydroxy-3-isopropylaminopropoxy)-1,4-dimethyl-2,3-indoledione hydrochloride have been found to have an $ED_{50}$ of 20, 26 and 49 μg/kg i.v., respectively, while propanolol, a well-known and widely used β-adrenergic blocking agent, has been found to have an $ED_{50}$ of 143 μg/kg i.v.

The compounds of formula I and their pharmaceutically acceptable acid addition salts may be used as medicaments in the form of pharmaceutical preparations which contain them in association with a compatible pharmaceutical carrier material. Such carrier material can be inert organic or inorganic carrier material which is suitable for parenteral or enteral, for example, oral administration, examples of such carrier materials are water, gelatin, lactose, starches, magnesium stearate, talc, gum arabic, polyalkyleneglycols vegetable oils, petroleum jelly, and the like. The pharmaceutical preparations can be produced in a solid dosage form, for example, as tablets, dragess, suppositories or capsules or in a liquid dosage form, for example, as solutions, suspensions or emulsions. The pharmaceutical preparations can be subjected to conventional pharmaceutical operations such as sterilization. Further, the pharmaceutical preparations may contain conventional adjuvants, such as, preservatives, stabilizers, emulsifiers, flavor-improvers, wetting agents, salts for varying the osmotic pressure, buffers, and the like.

A compound of formula I or a pharmaceutically acceptable acid addition salt thereof may be administered to warm-blooded animals in an amount in the range of from approximately 1 mg/kg to 10 mg/kg per day in a single dose or in divided doses. It is understood that this dosage range is given by way of example only and that it can be varied upwards or downwards depending on factors such as the particular compound or salt being administered, the route of administration and the needs and requirements of the warm-blooded animal as determined by the attending physician.

The following Examples further illustrate the invention. All parts are by weight and all temperatures are in degrees centigrade, unless otherwise mentioned.

EXAMPLE 1

Preparation of
7-(3-tert.butylamino-2-hydroxypropoxy)-1-methyl-2,3-indoledione hydrochloride 5 g of 1-methyl-7-hydroxy-2,3-indoledione and 5.5 g of Amberlyst resin A-26 were suspended in 50 ml of epichlorohydrin, and the suspensin was heated to 60° C. while stirring for 6 hours. The resin was removed, and the filtrate was evaporated to dryness. The dark red oil obtained was chromatographed on a silica gel column using chloroform for the elution. Fractions containing the desired product were combined and evaporated to give 3.82 g of a red oil which slowly crystallized from hexane. This product was suspended, without further purification, in 100 ml of ethanol, and 16 ml of tert.butylamine were added to the suspension. After stirring at 20° C. for 2 days, the mixture was evaporated, and the residue was treated with ethanolic hydrogen chloride. After crystallization from ethanol, 1.25 g of 7-(3-tert.butylamino-2-hydroxypropoxy)-1-methyl-2,3-indoledione hydrochloride in the form of orange crystals having a melting point of 245°-247° C. were obtained.

The following compounds were prepared in an analogous manner:

7-(3-Tert.butylamino-2-hydroxypropoxy)-1,4-dimethyl-2,3-indoledione hydrochloride having a melting point of 258°-261° C.

7-(2-Hydroxy-3-isopropylminopropoxy)-1,4-dimethyl-2,3-indoledione hydrochloride having a melting point of 227°-228° C.

The 1-methyl-7-hydroxy-2,3-indoledione used as the starting material in the first paragraph of this Example can be prepared, for example, as follows:

(a) 25.3 ml of o-anisidine were dissolved in 300 ml of pyridine, and the solution was treater over a period of 0.5 hour at a temperature below 30° C. with 47 ml of trifluoroacetic anhydride. The mixture was left to stand at 20° C. for 3 hours and then added to 2 liters of water. The solid was removed by filtration and crystallized from water, and 29.5 g of N-trifuoroacetyl-o-anisidine were obtained in the form of a pink solid having a melting point of 42°-43° C.

(b) 55.25 g of N-trifluoroacetyl-o-anididine in 200 ml of acetone were reacted with 62 ml of methyl iodide and 65 g of potassium hydroxide under reflux for 0.5 hour. The mixture was evaporated to dryness, water was added, and the resulting mixture was heated under reflux for 2 hours in order to complete the hydrolysis. The base was extracted with ether and washed with water. 34.2 g of N-methyl-o-anisidine were obtained which solidified on standing and had a melting point of 28°-30° C.

(c) 52 g of N-methyl-o-anisidine in 600 ml of dry benzene were added dropwise to a stirred solution of 38 ml of oxalyl chloride in 400 ml of benzene at 50° C. After completion of the addition, the solution was stirred at reflux for 5 hours and then evaporated to dryness. The residue was dissolved in 300 ml of nitrobenzene, and the solution was heated to 160° C. for 7 hours under an atmosphere of nitrogen. The red solution was evaporated to dryness, and the residue was crystallized from ethanol, and 29.01 g of 1-methyl-7-methoxy-2,3-indoledione having a melting point of 173°-176° C. were obtained.

(d) 17 g of 1-methyl-7-methoxy-2,3-indoledione in 340 ml of methylene chloride were treated dropwise with 25.5 ml of boron tribromide in 255 ml of methylene chloride at −70° C. After completion of the addition, the mixture was stirred at 0° C. for 1 hour and then at 20° C. for 2 hours. Excess boron tribromide was quenched with methanol at −70° C., and the mixture was subsequently evaporated to dryness. The solid residue was treated with 170 ml of water, filtered and washed with water, and 14.86 g of 1-methyl-7-hydroxy-2,3-indoledione having a melting point of 154°-166° C. were obtained. This was used in the process without further purification.

EXAMPLE 2

Preparation of
1-benzyl-7-(3-tert.butylamino-2-hydroxypropoxy)-4-methyl-2,3-indoledione A mixture of 2.53 g of 1-benzyl-4-methyl-7-hydroxy-2,3-indoledione, 25 ml of epichlorohydrin and 2.53 g of Amberlyst resin A-26 was stirred at 20° C. for 2 days. The resin was removed, and the mixture was evaporated to dryness to give a red solid. A mixture of 17.62 g of the red solid and 88.8 ml of tert.butylamine in 200 ml of methanol was heated under reflux for 4.5 hours. Water was added, the methanol was removed by evaporation, and the product was extracted with methylene chloride and chromatographed on silica gel using chloroform and finally methanol/chloroform (20%) for the elution. The fractions containing the required product were combined and converted into the acid oxalate salt in isopropanol (5.8 g of base required 1.42 g of oxalic acid). After recrystallization from isopropanil/diethyl ether, 5.28 g of the acid oxalate salt of 1-benzyl-7-(3-tert.butylamino-2-hydroxypropoxy)-4-methyl-2,3-indoledione having a melting point of above 220° C. were obtained. Treatment of this salt with sodium hydroxide in methylene chloride and crystallization from cyclohexane yielded 2.9 g of the free base having a melting point of 125°–128° C.

The 1-benzyl-4-methyl-7-hyroxy-2,3-indoledione used as the starting material can be prepared, for example, as follows:

(a) A mixture of 10 g of 2-methoxy-5-methylaniline and 16.3 ml of benzaldehyde in 80 ml of methanol was heated under reflux for 6 hours. 2 g of sodium borohydride were added to the cooled solution while stirring, and the mixture was left to stand for 8 hours. After the addition of water and removal of the methanol, the product was taken up in ethyl acetate and washed with 2N hydrochloric acid and water. After removal of the ethyl acetate and crystallization of the residue of the residue from isopropanol, 6.48 g of N-benzyl-2-methoxy-5-methylaniline having a melting point of 50°–57.5° C. were obtained.

(b) 41.13 g of N-benzyl-2-methoxy-5-methylaniline in 400 ml of benzene were added dropwise over a period of 1 hour at 60° C. while stirring at 25.15 g of oxalyl chloride in 250 ml of benzene. After heating under reflux for 3 hours, the solvent was removed and replaced with nitrotoluene. The resulting mixture was heated to 160° C. for 5 hours under nitrogen. The red solid obtained after removal of the nitrotoluene was crystallized from isopropanol, and 24.99 g of 1-benzyl-4-methyl-7-methoxy-2,3-indoledione having a melting point of 149°–152° C. were obtained.

(c) 15.46 g of 1-benzyl-4-methyl-7-methoxy-2,3-indoledione and 74 g of pyridine hydrochloride were heated to 200° C. for 2.5 hours. The mixture was partitioned between methylene chloride and aqueous dimethyl sulfoxide. The organic layer was separated and evaporated to give 3.75 g of crude 1-benzyl-4-methyl-7-hydroxy-2,3-indoledione in the form of a red solid having a melting point of 255°–262° C.

The following examples illustrate typical pharmaceutical preparations containing the 2,3-indoledione derivatives provided by the present invention:

EXAMPLE A

Tablets containing the following ingredients can be prepared in a conventional manner:

| Ingredient | Per tablet |
|---|---|
| 7-(3-Tert.butylamino-2-hydroxypropoxy)-1-methyl-2,3-indoledione | 25 mg |
| Lactose | 103 mg |
| Starch | 61 mg |
| Magnesium stearate | 11 mg |
| Total weight | 200 mg |

EXAMPLE B

A capsule containing the following ingredients can be produced in a conventional manner:

| Ingredient | Per capsule |
|---|---|
| 7-(3-Tert.butylamino-2-hydroxypropoxy)-1,2-dimethyl-2,3-indoledione | 25 mg |
| Lactose | 106 mg |
| Starch | 20 mg |
| Talc | 9 mg |
| Total weight | 160 mg |

We claim:
1. A compound of the formula

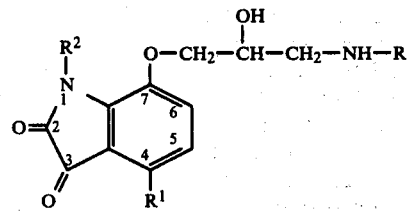

wherein R is isopropyl or tert.butyl, $R^1$ is hydrogen or lower alkyl, and $R^2$ is lower alkly, benzyl or β-phenethyl, or a pharmaceutically acceptable acid addition salt thereof.

2. A compound in accordance with claim 1, wherein $R^1$ is hydrogen, and $R^2$ is lower alkyl, or a pharmaceutically acceptable acid addition salt thereof.

3. A compound in accordance with claim 1, 7-(3-tert.butylamino-2-hydroxypropoxy)-1-methyl-2,3-indoledione.

4. A compound in accordance with claim 1, 7-(3-tert.butylamino-2-hydroxypropoxy)-1,4-dimethyl-2,3-indoledione.

5. A compound in accordance with claim 1, 7-(2-hydroxy-3-isopropylaminopropoxy)-1,4-dimethyl-2,3-indoledione.

6. A compound in accordance with claim 1, 1-benzyl-7-(3-tert.butylamino-2-hydroxypropoxy)-4-methyl-2,3-indoledione.

7. A compound of the formula

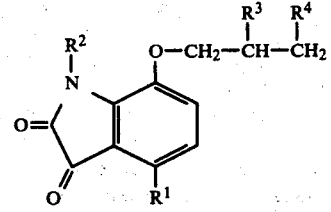

wherein $R^1$ is hydrogen or lower alkyl, $R^2$ is lower alkyl, benzyl or β-phenethyl, $R^3$ is hydroxy, and $R^4$ is chlorine or bromine, or $R^3$ and $R^4$, taken together, are oxygen.

* * * * *